(12) United States Patent
Sim et al.

(10) Patent No.: US 8,590,710 B2
(45) Date of Patent: Nov. 26, 2013

(54) TARGET PARTICLES-SEPARATING DEVICE AND METHOD USING MULTI-ORIFICE FLOW FRACTIONATION CHANNEL

(75) Inventors: Tae-seok Sim, Seoul (KR); Jeong-gun Lee, Seoul (KR); Hyo-il Jung, Seoul (KR); Ki-ho Kwon, Seoul (KR)

(73) Assignees: Samsung Electronics Co., Ltd., Suwon-si (KR); Industry-Academic Cooperation Foundation, Yonsei University, Seoul (KR)

( * ) Notice: Subject to any disclaimer, the term of this patent is extended or adjusted under 35 U.S.C. 154(b) by 232 days.

(21) Appl. No.: 13/156,630

(22) Filed: Jun. 9, 2011

(65) Prior Publication Data

US 2011/0303586 A1     Dec. 15, 2011

(30) Foreign Application Priority Data

Jun. 10, 2010   (KR) .................. 10-2010-0055112
Apr. 21, 2011   (KR) .................. 10-2011-0037353

(51) Int. Cl.
    *B07C 5/00*     (2006.01)

(52) U.S. Cl.
    USPC ............................. 209/644; 210/643; 435/4

(58) Field of Classification Search
    USPC ................. 209/643, 644; 210/643; 435/4
    See application file for complete search history.

(56) References Cited

U.S. PATENT DOCUMENTS

| | | | |
|---|---|---|---|
| 5,489,506 A * | 2/1996 | Crane ............................. | 435/2 |
| 2007/0026381 A1 | 2/2007 | Huang et al. | |
| 2008/0318324 A1 | 12/2008 | Chiu et al. | |
| 2009/0042310 A1 * | 2/2009 | Ward et al. ..................... | 436/154 |
| 2009/0078614 A1 * | 3/2009 | Varghese et al. ............... | 209/39 |
| 2009/0283456 A1 | 11/2009 | Le Vot et al. | |
| 2009/0283474 A1 | 11/2009 | Achard et al. | |
| 2011/0303586 A1 * | 12/2011 | Sim et al. ....................... | 209/268 |

FOREIGN PATENT DOCUMENTS

| | | |
|---|---|---|
| KR | 10-2005-0074214 A | 7/2005 |
| KR | 10-2008-0052036 A | 6/2008 |
| WO | 2008157220 A1 | 12/2008 |
| WO | WO 2009/115575 A1 | 9/2009 |
| WO | 2009140326 A2 | 11/2009 |

OTHER PUBLICATIONS

"Multistage-multiorifice flow fractionation (MS-MOFF): continuous size-based separation of microspheres using multiple series of contraction/expansion microchannels," Tae Seok Sim, et al., Lab Chip, 2011, 11, 93.

(Continued)

*Primary Examiner* — Terrell Matthews
(74) *Attorney, Agent, or Firm* — Leydig, Voit & Mayer, Ltd.

(57) ABSTRACT

A device separating target particles in a fluid sample includes first through third multi-orifice flow fractionation ("MOFF") channels, each including a multi-orifice segment with an inlet and an outlet at opposite ends, and an alternating series of contraction channels and expansion chambers interconnected in a lengthwise direction; a first separation unit including a first separation channel which is interconnected in fluid communication with a center region of the outlet of the first MOFF channel, and first branch channels which are interconnected in fluid communication with sidewall regions of the outlet of the first MOFF channel, and respectively with inlets of the second and third MOFF channels; and buffer inlets which are connected to the inlets of the second and third MOFF channels and through which a buffer flows into the second and third MOFF channels.

14 Claims, 12 Drawing Sheets

(56) References Cited

OTHER PUBLICATIONS

"Multiorifice Flow Fractionation: Continuous Size-Based Separation of Microspheres Using a Series of Contraction/Expansion Microchannels," Jae-Sung Park, et al., Anal. Chem., 2009, 81, 8280-8288.

"Microfluidic Chip for Bio-particle Separation using Hydrodynamic Forces Induced by Multi-orifice Microchannel," Jae Sung Park et al. Transations of the Korean Society of Mechanical Engineers(KSME) B, 2008, pp. 273-274.

Park et al., "Continuous Focusing of Microparticles Using Inertial Lift Force and Vorticity via Multi-orifice Microfluidic Channels," *Lab Chip*, 2009, 9, 939-948.

* cited by examiner

TARGET PARTICLES-SEPARATING DEVICE AND METHOD USING MULTI-ORIFICE FLOW FRACTIONATION CHANNEL

CROSS-REFERENCE TO RELATED APPLICATIONS

This application claims priority to Korean Patent Application No. 10-2010-0055112, filed on Jun. 10, 2010, and Korean Patent Application No. 10-2011-0037353, filed on Apr. 21, 2011, and all the benefits accruing therefrom under 35 U.S.C. §119, the disclosures of which are incorporated herein by reference.

BACKGROUND

1. Field

Provided is a device and method for separating target particles in a fluid sample by size.

2. Description of the Related Art

Technologies for separating target particles in a fluid sample have applications in various fields. For example, diverse medical fields associated with phathogen detection, new drug discovery, drug tests, cell replacement therapies, and the like necessitate target cell separation. In environmental fields associated with sewage treatment, technologies of separating fine source contaminants may have a wide range of applications. In cancer diagnosis, early detection of tumor cells and monitoring after surgical operations is a very crucial factor, so there has been extensive research for more convenient and accurate cancer cell separation technologies. However, due to being complicated and time-consuming, existing cancer cell separation technologies are ineffective in treating cancer related diseases that necessitate rapid diagnosis and treatment. For example, circulating tumor cells ("CTCs") in breast cancer are rare in the body, and thus, sampling a sufficient amount of CTCs for medical treatment and research is difficult. Therefore, there has been a demand for efficient technologies of separating target particles such as cancer cells present in a small amount in a fluid sample containing body fluids such as blood.

SUMMARY

Provided are a device and method of efficient separation of target particles in a fluid sample by using a multi-orifice flow fractionation ("MOFF") channel.

Embodiments will be set forth in part in the description which follows and, in part, will be apparent from the description, or may be learned by practice of the presented embodiments.

Provided is a device for separating target particles in a fluid sample, the device including a first, second and third MOFF channels, each including a multi-orifice segment with an inlet and an outlet at opposite ends, the multi-orifice segment including an alternating series of contraction channels and expansion chambers interconnected in a lengthwise direction, the dimensions of the contraction channels and expansion chambers defined based on a size of the target particles; a first separation unit including a first separation channel which is interconnected in fluid communication with a center region of the outlet of the first MOFF channel, and first branch channels which are interconnected in fluid communication with sidewall regions of the outlet of the first MOFF channel and respectively with inlets of the second and third MOFF channels; and buffer inlets which are connected to the inlets of the second and third MOFF channels and through which a buffer flows into the second and third MOFF channels.

The first separation channel may have a relatively large fluidic resistance compared to a fluidic resistance of the first branch channels, the fluid resistances determined by the dimensions of the first separation channel and the first branch channels.

A cross-sectional area of the first separation channel may be relatively small compared to a cross-sectional area of the first branch channels.

The device may further include a second separation unit including a second separation channel which is interconnected in fluid communication with a center region of the outlet of each of the second and third MOFF channels, and second branch channels which are interconnected in fluid communication with a sidewall region of the outlet of each of the second and third MOFF channels.

The device may further include waste chambers which are interconnected in fluid communication with the second branch channels, such that the waste chambers collect non-selected particles excluding the target particles in the fluid sample.

The device may further include a sample inlet which is interconnected in fluid communication with the inlet of the first MOFF channel, and through which the fluid sample is introduced.

The device may further include one target particle via which is interconnected in fluid communication with the first and second separation channels, and in which the target particles in the fluid sample are collected.

The fluidic resistance of the first separation channel is about five times as large as a fluidic resistance of each of the first, second, and third MOFF channels, the fluid resistances based on dimensions of the first separation channel and the first, second, and third MOFF channels.

According to another aspect of the present invention, a method of separating target particles in a fluid sample includes providing a plurality of MOFF channels, each including a multi-orifice segment with an inlet and an outlet at opposite ends, the multi-orifice segment including an alternating series of contraction channels and expansion chambers interconnected in a lengthwise direction, the dimensions of the contraction channels and expansion chambers are defined based on a size of the target particles; introducing a first fluid sample including the target particles into the inlet of a first MOFF channel; collecting target particles discharged from a center region of the outlet of the first MOFF channel to separate the target particles; introducing a second fluid sample discharged from sidewall regions of the outlet of the first MOFF channel into the inlet of a second MOFF channel; and collecting target particles discharged from a center region of an outlet of the second MOFF channel to separate the target particles.

The introducing the second fluid sample discharged from the sidewall regions of the outlet of the first MOFF channel into the inlet of the second MOFF channel may include introducing a buffer into the inlet of the second MOFF channel so that a total fluid quantity introduced into the inlet of the second MOFF channel is consistent with a quantity of the first fluid sample introduced into the inlet of the first MOFF channel.

The introducing the second fluid sample discharged from the sidewall region of the outlet of the first MOFF channel into the inlet of the second MOFF channel may further include introducing a buffer into the inlet of the second MOFF channel so that a total fluid quantity introduced into the inlet of the second MOFF channel is different from a quantity of the first fluid sample introduced into the inlet of the first MOFF channel.

BRIEF DESCRIPTION OF THE DRAWINGS

These and/or other features will become apparent and more readily appreciated from the following description of the embodiments, taken in conjunction with the accompanying drawings of which:

FIG. 2 illustrates an embodiment of a method of separating target particles in a fluid sample with a plurality of MOFF channels, according to the present disclosure;

DETAILED DESCRIPTION

Figure 1A:
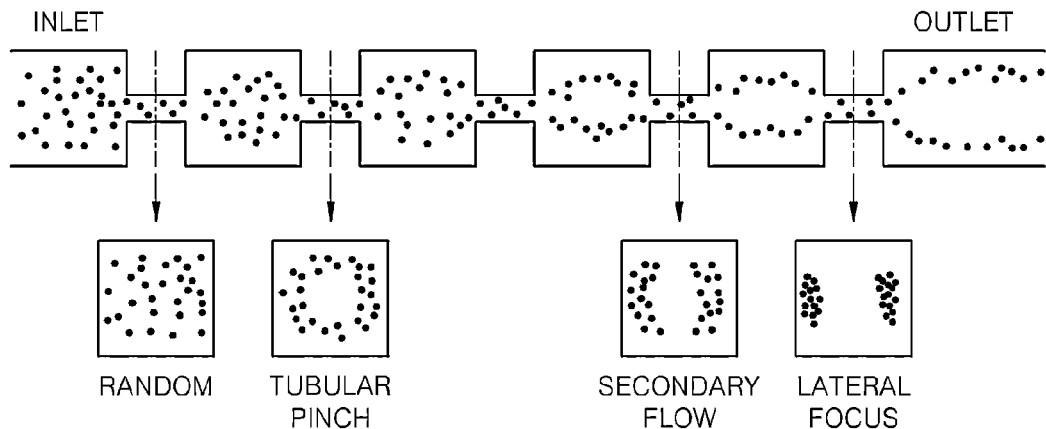
FIG. 1A illustrates an embodiment of focusing of target particles by force exerted in a multi-orifice segment including an alternating series of contraction channels and expansion chambers interconnected in a lengthwise direction, where the dimensions of the contraction channels and expansion chambers are defined based on a size of the target particles.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, "connected" includes physically and/or fluidly connected. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

Figures 1, 1B:
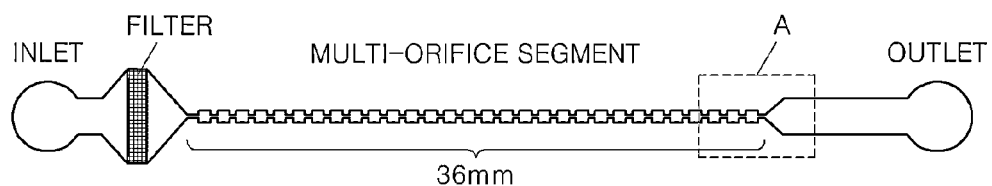
FIGS. 1B-1 and 1B-2 illustrates a schematic structure of an embodiment of a multi-orifice flow fractionation ("MOFF") channel, according to the present disclosure.
Figures 1, 1B, 2:
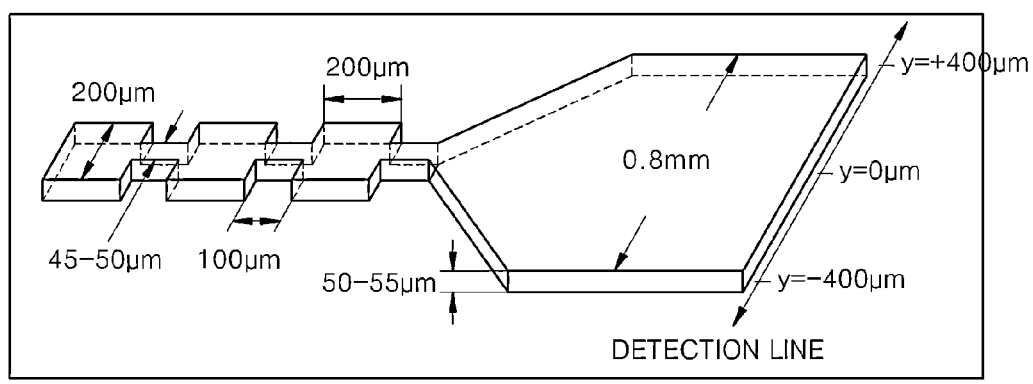
Figure 1C:
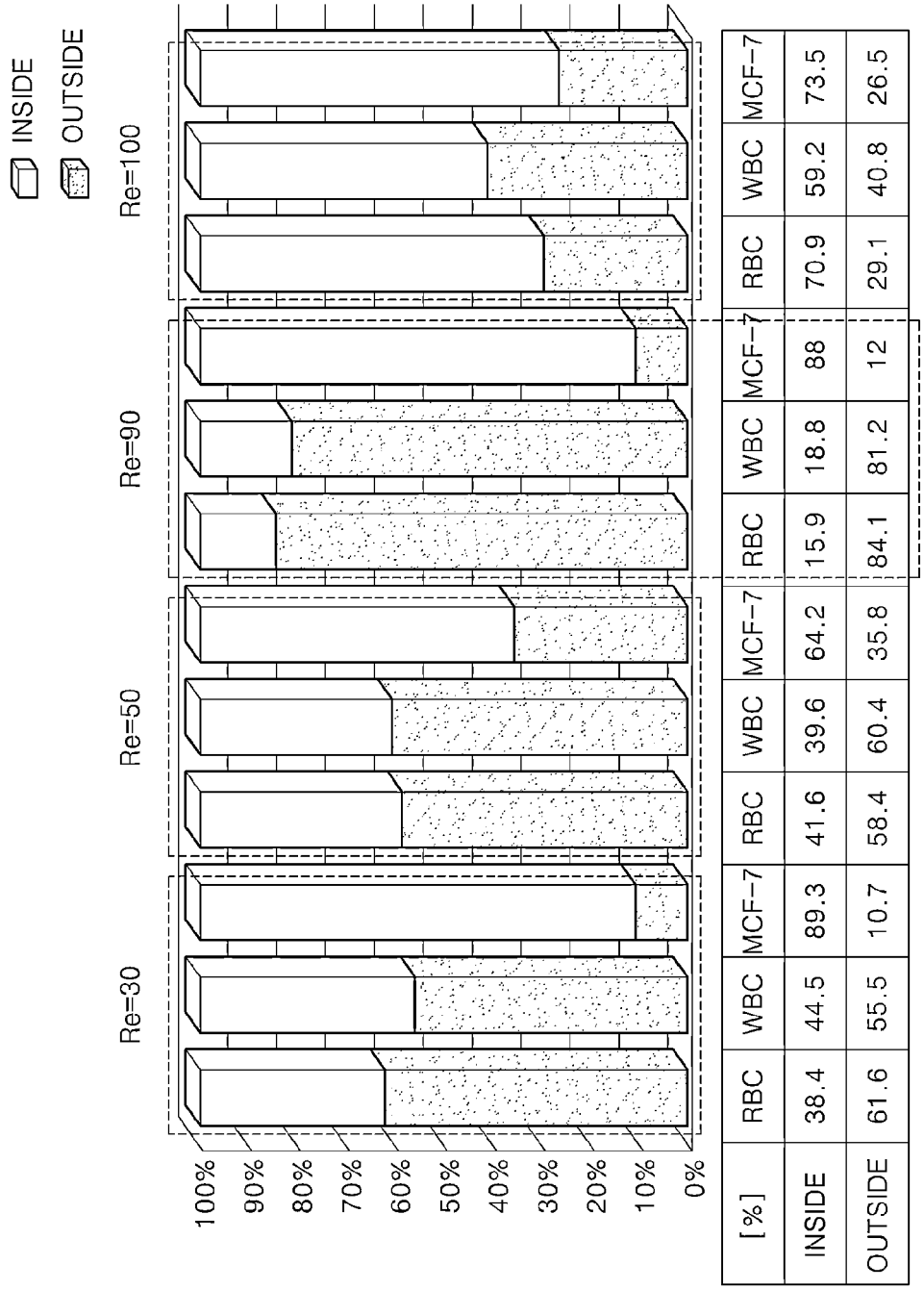
FIG. 1C illustrates the results of an embodiment of separating particles of various sizes by using a single MOFF channel according to the present disclosure.
Figure 2:
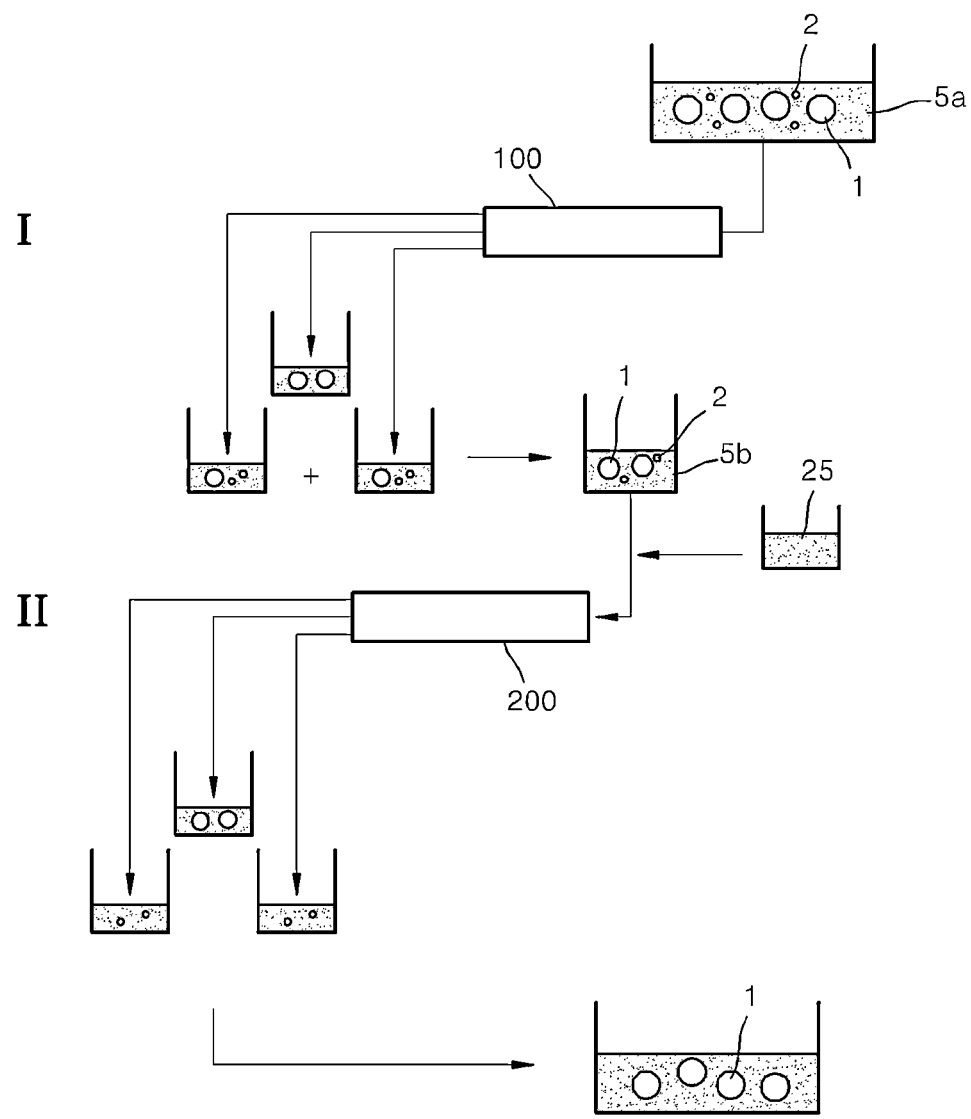

FIG. 1A illustrates an embodiment of focusing of target particles by force exerted in a multi-orifice segment including an alternating series of contraction channels and expansion chambers interconnected in a lengthwise direction, where the dimensions of the contraction channels and the expansion chambers are defined based on the size of the target particles. FIGS. 1B-1 and 1B-2 illustrate a schematic structure of an embodiment of a multi-orifice flow fractionation ("MOFF") channel, according to the present disclosure. FIG. 1C illustrates the results of an embodiment of separating particles of various sizes by using a single MOFF channel according to the present disclosure.

In microfluidics, physical phenomena in fluid and particle behaviors are analyzed using dimensionless numbers. In general, the dimensionless number refers to a Reynolds number (Re) defined as a ratio of viscous force and inertial force. The behavior of particles of a fluid is influenced by inertial and viscous forces driven by contact with the fluid. The Reynolds number (Re) is determined by an average flow rate, a characteristic length, a kinematic viscosity, a dynamic viscosity, a viscous coefficient, and a density of the fluid that may affect the inertial and viscous forces. The Reynolds number (Re) may be of use for predicting whether a particular fluid is in a laminar flow or a turbulent flow. Laminar flow refers to a streamline flow of fluid in layers, while turbulent flow refers to an irregular motion of fluid leading to mixing. Laminar flow is a viscous force-dominant flow having a low Reynolds number (Re) in calm and constant motion of a fluid. Turbulent flow is an inertia force-dominant flow having a high Reynolds number (Re) in random fluctuation of a flow. Fluidic motions are mostly in turbulent flow, but may lead to a laminar flow when a high viscous fluid slowly passes along a narrow channel, for example, as when a blood sample passes a channel in a microfluidic device.

Referring to FIG. 1A, until a fluid that has entered through an inlet passes a first expansion region and a first contraction region, and reaches a second expansion region, particles in the fluid are not seriously influenced by the flow of the fluid and are randomly distributed in the fluid (see FIG. 1, denoted by "Random"). Successive passing through the multiple expansion and contraction regions may cause the particles in the fluid to redistribute in a circular pattern due to a tubular pinch effect (see FIG. 1A, denoted by "Tubular pinch"). Afterwards, the particles in the fluid are influenced by a force driven by a secondary flow along a surface of a channel (see FIG. 1A, denoted by "Secondary flow"), and thus, the particles are focused on opposite side walls of the channel toward an outlet (see FIG. 1A, denoted by "Lateral focus"). In the multi-orifice segment of FIG. 1A, the behavior of particles varies depending on a relative dimensional ratio of particles to a cross-section of the channel, which indicates that the particles in the fluid may be separated by size using the multi-orifice segment.

Referring to FIGS. 1B-1 and 1B-2, which are a schematic and enlarged view of an embodiment of a MOFF channel according to present disclosure using the multi-orifice segment of FIG. 1A. FIG. 1B-2 illustrates portion A of FIG. 1B-1 denoted by the dotted line outline. The MOFF channel is an example of a microfluidic device for continuously separating particles in fluid by size. In particular, the MOFF channel may include the multi-orifice segment including an alternating series of contraction channels and expansion chambers interconnected in a lengthwise direction, where the dimensions of the contraction channels and the expansion chambers are defined based on the size of target particles. The length and cross-section of the contraction channels and expansion chambers may vary depending on the size of target particles in fluid. The number of contraction channels and expansion chambers may vary. Opposite ends of the multi-orifice segment may be interconnected respectively to an inlet (see FIG. 1B-1, denoted by "INLET") through which a fluid sample is introduced, such as by injection, and an outlet (see FIG. 1B-1, denoted by "OUTLET") through which particles in the fluid sample that are separated by size are discharged. A filter (see FIG. 1B-1, denoted by "FILTER") may be disposed between the inlet of the MOFF channel and the multi-orifice segment. The filter may filter out impurities in the fluid sample. The outlet of the MOFF channel may have a structure that is long in a direction in which the fluid sample flows, relative to the contraction channels and expansion chambers of the multi-orifice segment. The outlet of the MOFF channel may include a detection line (see FIG. 1B-2, denoted by "DETECTION LINE") for identifying whether the particles are separated by size.

Particular figures and units in FIG. 1B-2 are only for illustrative purposes and not to limit the dimensions and cross-sectional areas of the MOFF channel. In FIG. 1B-2, dimensions range from several micrometers (μm) to several millimeters (mm).

FIG. 1C illustrates experimental results of an embodiment of separating target particles in a fluid sample with the single MOFF channel of FIGS. 1B-1 and 1B-2, in which the fluid sample was blood and the target particles were MCF-7 cells (human breast adenocarcinoma cells) present in the blood. The MCF-7 cells are circulating tumor cells ("CTCs") present in blood. Separating MCF-7 cells from white and red blood cells in blood is a technology applied for cancer diagnosis. As for a cancer patient, whether metastatic cancer cells remain or not after a surgical treatment on the cancer is an influential factor to the mortality rate of the patient. Thus, accurately detecting even a CTC present among about $10^9$ red blood cells completely is very crucial to improve the survival rate before and after a treatment to a cancer patient.

In general, every cancer patient is subjected to anticancer treatment following a surgical operation for a higher survival rate, thus being physically or mentally distressed from vomiting, hair loss, or reduced immunity, even though it may not be necessarily for surgical patient to undergo the anticancer treatment, which leads to an unnecessary waste of medical resources and an economical loss. Accurate detection of the number of CTCs in blood enables a determination of whether metasis has occurred or a degree of the metasis, thereby leading to reduced side effects of such an anticancer treatment. Furthermore, with separated CTCs, a customized treatment that suits a patient may be provided. Accurate detection of the number of CTCs in blood necessitates a target particle separation technology satisfying basic requirements in throughput, which indicates the number of cells separated per unit time, recovery of separated target cells to introduced target cells, and purity of the separated target cells.

As described above, as a fluid sample passes through the MOFF channel, particles in the fluid sample may be separated by size in a range of Reynolds numbers (Re). In one embodiment, for example, if the Reynolds numbers (Re) range from about 60 to about 90, relatively large particles (for example, about 15 μm or greater) are distributed near a center line (see FIG. 1C, denoted by "Inside") of the outlet of the MOFF channel, while relatively small particles (for example, about 7 μm or less) are distributed near opposite sides (see FIG. 1C, denoted by "Outside") of the outlet of the MOFF channel. FIG. 1C illustrates the results of an embodiment of separating red blood cells (having a diameter of about 5 μm), white blood cells (having a diameter of about 10 μm), and MCF-7 cells (having a diameter of about 20 μm) with the MOFF channel of FIGS. 1B-1 and 1B-2 at various Reynolds numbers (Re) of about 30, 50, 90, and 100, which are selected based on the sizes of target particles and channels.

Referring to FIG. 1C, the numbers of cells near the center and sidewall regions of the MOFF channel are different according to the Reynolds numbers (Re). With a Reynolds number of 90 (Re=90), the recovery of the MCF-7 cells is very as high at about 88% in the center region ("Inside") of the MOFF channel, compared to in the sidewall regions ("Outside"), while the recoveries of the red blood cells ("RBC") and the white blood cells ("WBC") are rather very as small at about 15.9% and 18.9%, respectively, in the center region of the MOFF channel, compared to in the sidewall regions. Therefore, by separating the particles distributed in the center region of the MOFF channel, about 88% of CTCs present in blood may be isolated. Although, as described above, target particles may be separated with a high yield with the MOFF channel having an optimal Reynolds number (Re) that suits to a size of the target particles, there may be a need to further improve the recovery of target particles. As illustrated, for example, by using a single MOFF channel having an optimal Reynolds number (Re=90), about 88% of CTCs (about 20 μm) present in blood may be separated. However, this recovery has a limitation to be applied to cancer diagnosis and treatment. To improve the recovery of target particles using a single MOFF channel, a device and method of separating target particles with a plurality of MOFF channels have been proposed.

FIG. 2 illustrates an embodiment of a method of separating target particles in a fluid sample with a plurality of MOFF channels, according to the present disclosure.

According to the illustrated embodiment, the method may include: providing a plurality of MOFF channels, each including a multi-orifice segment with an inlet and outlet at opposite ends, the multi-orifice segment including an alternating series of contraction channels and expansion chambers interconnected in a lengthwise direction, where the dimensions of the contraction channels and expansion chambers are defined based on the size of the target particles; introducing a first fluid sample including target particles into an inlet of a first MOFF channel of the plurality of MOFF channels; collecting target particles discharged from a center region of an outlet of the first MOFF channel (First separation step, denoted by "I"); introducing a second fluid sample discharged from sidewall regions of the outlet of the first MOFF channel into an inlet of a second MOFF channel of the plurality of MOFF channels; and collecting target particles discharged from a center region of an outlet of the second MOFF channel (Second separation step, denoted as "II").

In the providing of the plurality of MOFF channels, each including a multi-orifice segment with an inlet and outlet at opposite ends, the multi-orifice segment including an alternating series of contraction channels and expansion chambers interconnected in a lengthwise direction, where the dimensions of the contraction channels and expansion chambers are defined based on the size of the target particles, MOFF channels 100 and 200 each having a constant optimal Reynolds number (Re) according to a known size of target particles 1 and a flow quantity of a first fluid sample 5a may be manufactured. As described above, the MOFF channels 100 and 200 having a constant optimal Reynolds number (Re) may have an increased recovery of the target particles. The MOFF channels 100 and 200 may be implemented to have the same structure and length.

In the introducing of the first fluid sample 5a including the target particles 1 into an inlet of the first MOFF channel 100 of the plurality of MOFF channels, the first fluid sample 5a may be injected into the inlet of the first MOFF channel 100 by using a syringe (not shown) or pump (not shown). Referring to FIG. 2, the first fluid sample 5a includes remnants 2 of the target particles 1. The remnants 2 may have various sizes. In the embodiment of FIG. 2, the remnant 2 may have at least a smaller size than a target particle 1. In some embodiments, the first fluid sample 5a may be blood, the target particles 1 may be MCF-7 cells, and the remnants 2 may be red blood cells and/or white blood cells.

In the first separation step I of collecting the target particles 1 discharged from the center region of the outlet of the first MOFF channel 100, the target particles 1 cluster in the center region of an outlet of the first MOFF channel 100, and are then collected, thus being primarily separated from the first fluid sample 5a. In this step, the target particles 1 may be separated with a maximum recovery by using only one MOFF channel, namely the first MOFF channel 100. The remnants 2 and the remaining target particles 1, not separated in the first separation step I, cluster in the sidewall regions of the outlet of the first MOFF channel 100, and are subsequently separated in the second separation step II, which will be described in detail below. In some embodiments, in the first separation step I, about 88% of the MCF-7 cells present in blood may be separated, while about 12% of the MCF-7 cells remain not separated. The non-separated 12% of MCF-7 cells is expected to concentrate in the sidewall regions of the outlet of the first MOFF channel 10, which are collected along with the remnant 2 in the second separation step II, which will be described in detail below.

In the introducing of a second fluid sample 5b discharged from the sidewall regions of the outlet of the first MOFF channel 100 into an inlet of the second MOFF channel 200, the second fluid sample 5b may include the remaining target particles 1 not separated in the first fluid sample 5a in the first separation step I, and the remnants 2. The second fluid sample 5b may have a smaller flow quantity than the first fluid sample 5a because the second fluid sample 5b is a product of the primary separation of the target particles 1 from the first fluid sample 5a. As described above, the MOFF channels 100 and 200 are manufactured to have an optimal constant Reynolds number (Re) in consideration of a flow quantity of the first fluid sample 5a. Thus, to separate the target particles 1 in the same conditions, a flow quantity into another MOFF channel, namely, the second MOFF channel 200, needs to be the same as that into the first MOFF channel 100. In some embodiments, the introducing of the second fluid sample 5b into the inlet of the second MOFF channel 200 may further include introducing a buffer 25 into the inlet of the second MOFF channel 200 so that a quantity of the fluid introduced into the inlet of the second MOFF channel 200, including the second fluid sample 5b and the buffer 25, is equal to the quantity of the first fluid sample 5a introduced into the inlet of the first MOFF channel 100. In the introducing of the second fluid sample 5b discharged from the sidewall regions of the outlet of the first MOFF channel 100 into the inlet of the second MOFF channel 200, as described above, the second fluid sample 5b and the buffer 25 may be introduced together into the inlet of the second MOFF channel 200.

In one embodiment, the introducing of the second fluid sample 5b discharged from the sidewall regions of the outlet of the first MOFF channel 100 into the inlet of the second MOFF channel 200 may further include introducing the buffer 25 into the inlet of the second MOFF channel 200 so that a quantity of the fluid introduced into the inlet of the second MOFF channel 20, including the second fluid sample 5b and the buffer 25, is different from the quantity of the first fluid sample 5a introduced into the inlet of the first MOFF channel 100. Herein, the quantity of the buffer 25 may be adjusted to separate particles of different sizes in the first fluid sample 5a. In one embodiment, for example, when the quantity of the buffer 25 is adjusted to change the quantity of the fluid introduced into the inlet of the second MOFF channel 200 to be different from that of the first fluid sample 5a introduced into the inlet of the first MOFF channel 100, the first MOFF channel 100 and the second MOFF channel 200 may have different flow qpantities, and thus different Reynolds numbers (Re). As a result, the sizes of particles discharged from the center region and/or the sidewall regions of the first MOFF channel 100 are different from those of the second MOFF channel 200 so that particles of different sizes in the first fluid sample 5a may be separated passing through the first MOFF channel 100 and the second MOFF channel 200.

In the second separation step II of collecting the target particles 1 discharged from the center region of an outlet of the second MOFF channel 200, the target particles 1 cluster in the center region of the outlet of the second MOFF channel 200, and are collected, thus being secondarily separated from the second fluid sample 5b. In this step, the target particles 1 may be separated with a maximum recovery by using one MOFF channel, namely, the second MOFF channel 200, as first MOFF channel 100. The remnants 2 and the remaining target particles 1, not separated in the second separation step II, cluster in the sidewall regions of the outlet of another MOFF channel, and are separated in a third separation step III (not shown). In one embodiment, for example, about 88% of the MCF-7 cells present in blood may be separated in the first separation step I, and about 12% of the MCF-7 cells remaining not separated in the first separation step I may be separated with a yield of about 88% in the second separation step II. Thus, about 98.56% (88%+12%×0.88) of the MCF-7 cells may be separated from the initial blood sample. When successive separation steps, including a third separation step, are performed, the target particles may be separated with a yield of nearly 100%.

Figure 3:
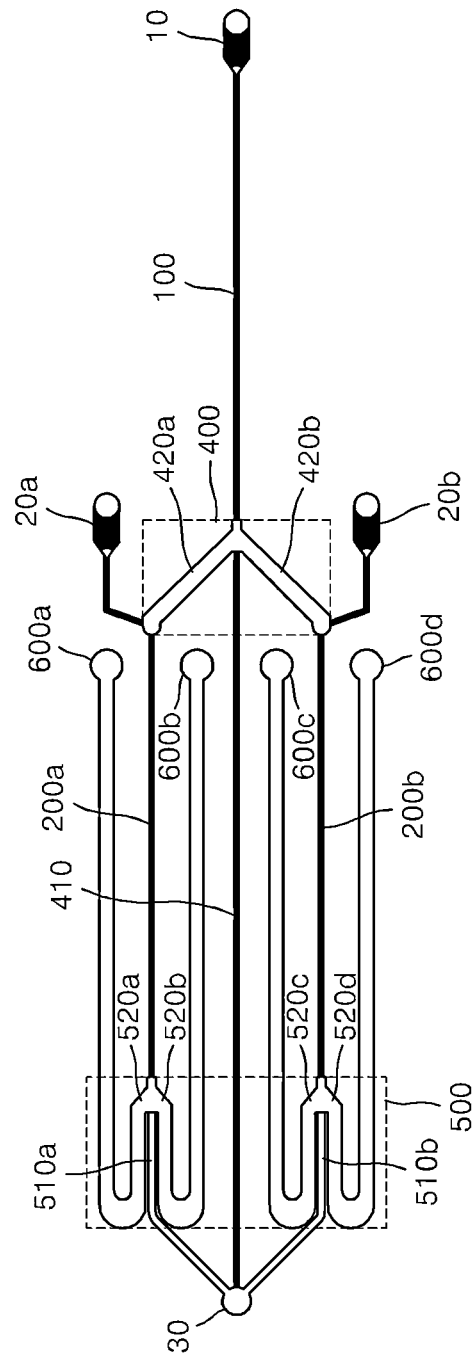
FIG. 3 illustrates an embodiment of a device for separating target particles in a fluid sample with a plurality of MOFF channels, according to the present disclosure.

FIG. 3 illustrates an embodiment of a device for separating target particles in a fluid sample with a plurality of MOFF channels, according to the present disclosure.

Referring to FIG. 3, the target particles-separating device may include at least three MOFF channels, namely, first, second, and third MOFF channels 100, 200a, and 200b, each including a multi-orifice segment with an inlet and outlet at opposite ends, the multi-orifice segment including an alternating series of contraction channels and expansion chambers interconnected in a lengthwise direction, where the dimensions of the contraction channels and expansion chambers are defined based on the size of target particles; and a first separation unit 400 including a first separation channel 410 and first branch channels 420a and 420b, the first separation channel 410 interconnected in fluid communication with a center region of an outlet of the first MOFF channel 100, the first branch channels 420a and 420b interconnected in fluid communication with the sidewall regions of the outlet of the first MOFF channel 100 and respectively with the inlets of the second and third MOFF channels 200a and 200b.

The target particles-separating device may include buffer inlets 20a and 20b in at least a region of the inlets of the respective second and third MOFF channels 200a and 200b to allow a buffer flow into the second and third MOFF channels 200a and 200b. A detailed description of the first, second, and third MOFF channels 100, 200a, and 200b is provided above with reference to FIG. 1. As described with reference to FIG. 1, the first, second, and third MOFF channels 100, 200a, and 200b may each include a multi-orifice segment including an alternating series of contraction channels and expansion chambers interconnected in a lengthwise direction, where the dimensions of the contraction channels and expansion chambers are defined based on the size of target particles, and may be designed to have an optimal constant Reynolds number (Re) according to a size of target particles and a flow quantity of a fluid sample. In one embodiment, for example, the first, second, and third MOFF channels 100, 200a, and 200b for separating MCF-7 cells present in blood may each have a constant specific Reynolds number (for example, Re=about 90), and may allow focusing of particles having a size of about 15 μm in their center region and particles having a size of about 7 μm in their sidewall regions, thus separating particles having different sizes with optimal recoveries. In some embodiments, the outlet of the first MOFF channel 100 may be interconnected in fluid communication with the inlets of the second and third MOFF channels 200a and 200b. The target particles in the fluid sample may be repeatedly separated using each of the separate single first, second, and third MOFF channels 100, 200a, and 200b.

Referring to FIG. 3, the target particles-separating device may further include the first separation unit 400 including the first separation channel 410 that is interconnected in fluid communication with the center region of the outlet of the first MOFF channel 100. As the fluid sample is introduced into the first MOFF channel 100, while passing through the first MOFF channel 100, relatively large target particles present in the fluid sample are concentrated in the center region of the outlet of the first MOFF channel 100, and are driven by fluid pressure to travel further along the first separation channel 410 interconnected in fluid communication with the center region of the outlet of the first MOFF channel 100. Referring to FIG. 3, the first separation unit 400 may further include the first branch channels 420a and 420b interconnecting the sidewall regions of the outlet of the first MOFF channel 100 in fluid communication with the inlets of the second and third MOFF channels 200a and 200b, respectively.

As the fluid sample is introduced into the first MOFF channel 100, while passing through the first MOFF channel 100, relatively small target particles present in the fluid sample are concentrated on the sidewall regions of the outlet of the first MOFF channel 100, and are driven by fluid pressure to travel further along the first branch channels 420a and 420b interconnected in fluid communication with the sidewall regions of the outlet of the first MOFF channel 100. In this case, some remaining target particles, not having flowed into the first separation channel 410, may flow into the first branch channels 420a and 420b. Referring to FIG. 3, the first branch channels 420a and 420b respectively connect one of the sidewall regions of the outlet of the first MOFF channel 100 in fluid communication with the inlet of the second MOFF channel 200a, and the other sidewall region of the outlet of the first MOFF channel 100 in fluid communication with the inlet of the third MOFF channel 200b. Thus, as the fluid sample including the target particles passes through the first MOFF channel 100 and some target particles in the fluid sample flow into the first separation channel 410, the target particles may be primarily separated.

Once the fluid sample passes the first MOFF channel 100, the flow quantity of the fluid sample entering the second MOFF channel 200a and the third MOFF channel 200b may be reduced due to a reduced fluid pressure by friction in the first MOFF channel 100 and a branch structure of the first separation unit 400, including the first separation channel 410 and the first branch channels 420a and 420b, and a change in fluid flow such as a back flow caused from a fluidic resistance change may occur. Referring to FIG. 3, to maintain the flow quantity of the fluid sample entering the second MOFF channel 200a and the third MOFF channel 200b to be consistent with that of the fluid sample entering the first MOFF channel 100, the inlets of the second and third MOFF channels 200a and 200b may be connected in fluid communication with the buffer inlets 20a and 20b for guiding a buffer to flow into the second and third MOFF channels 200a and 200b. Thus, at the time when the fluid sample flows into the second and third MOFF channels 220a and 220b from the first separation unit 400, a buffer may be supplied from the buffer inlets 20a and 20b to adjust the flow quantity and flow rate of the fluid sample in the second and third MOFF channels 220a and 220b to be consistent with those of the fluid sample entering the first MOFF channel 100.

Figure 4:
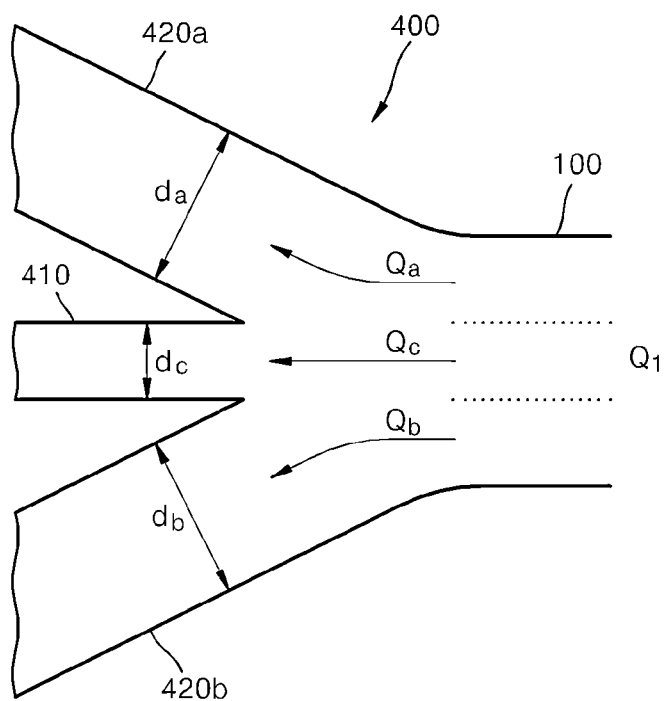
FIG. 4 illustrates an embodiment of a structure of a first separation unit of a target particles-separating device, according to the present disclosure.
Figure 5:
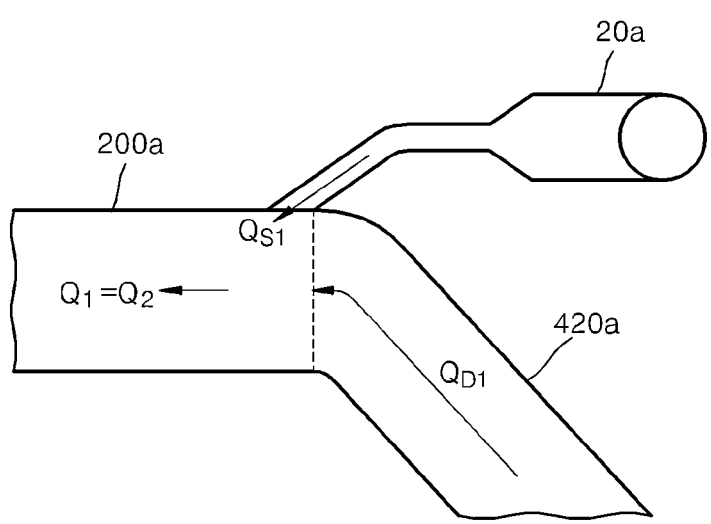
FIG. 5 illustrates an embodiment of a buffer inlet interconnected in fluid communication with an inlet of a second MOFF channel of a target particles-separating device, according to the present disclosure.

In the illustrated embodiment, for example, referring to FIG. 5, a flow quantity $Q_{D1}$ of the fluid sample in the first branch channel 420a is less than a flow quantity $Q_1$ (FIG. 4) of the fluid sample in the first MOFF channel 100. A change in flow rate may occur while the fluid sample passes through the first separation unit 400. However, as a buffer is supplied from the buffer inlet 20a connected to the inlet of the second MOFF channel 200a at a constant flow rate in a constant quantity $Q_{S1}$ at a constant flow rate, the reduced flow rate and flow quantity $Q_{D1}$ of the fluid sample in the first branch channel 420a may be compensated for so that the flow rate and flow quantity $Q_2$ in the second MOFF channel 200a are maintained consistent with the flow rate and flow quantity $Q_1$ of the fluid sample in the first MOFF channel 100.

In another embodiment, at the time when the fluid sample flows into the second and third MOFF channels 220a and 220b through the first separation unit 400, a buffer may be supplied from the buffer inlets 20a and 20b to adjust the flow quantity and flow rate of the fluid sample in the second and third MOFF channels 220a and 220b to be different from those of the fluid sample entering the first MOFF channel 100. In one embodiment, for example, referring to FIG. 5, a flow quantity $Q_{D1}$ of the fluid sample in the first branch channel 420a is less than a flow quantity $Q_1$ (FIG. 4) of the fluid sample in the first MOFF channel 100. A change in flow rate may occur while the fluid sample passes the first separation unit 400. However, as a buffer is supplied from the buffer inlet 20a connected to the inlet of the second MOFF channel 200a at a constant flow rate in a constant flow quantity $Q_{S1}$, the reduced flow rate and flow quantity $Q_{D1}$ of the fluid sample in the first branch channel 420a may be compensated for so that the flow rate and flow quantity $Q_2$ in the second MOFF channel 200a is different from the flow rate and flow quantity $Q_1$ of the fluid sample in the first MOFF channel 100.

Referring to FIG. 3, dimensions of the first separation channel 410 may be determined such that the first separation channel 410 has a relatively large fluidic resistance compared to a fluidic resistance determined by the dimensions of the first branch channels 420a and 420b. A cross-sectional area of the first separation channel 410 may be relatively small compared to that of the first branch channels 420a and 420b. After determination of the cross-sectional area and fluidic resistance of the first separation channel 410, a cross-sectional area and a fluidic resistance of each of the first branch channels 420a and 420b may be defined based on the cross-sectional area and fluidic resistance of the first separation channel 410, so as to suppress a change in fluid flow such as a back flow into the first separation unit 400 and have a stable inflow of the fluid sample into the second and third MOFF channels 200a and 200b. In one embodiment, for example, referring to FIG. 4, the flow quantity $Q_1$ of the fluid sample in the first MOFF channel 100 may be defined as a sum of individual laminar flows of target particles in the fluid sample with particular sizes, for example, a sum of a laminar flow $Q_c$ in the center region of the outlet of the first MOFF channel 100, and laminar flows $Q_a$ and $Q_b$ in the sidewall regions of the outlet of the first MOFF channel 100. The laminar flow $Q_c$ in the center region may flow into the first separation channel 410, and the laminar flows $Q_a$ and $Q_b$ in the sidewall regions may flow into the first branch channels 420a and 420b, respectively. The branched channel structure causes changes in fluidic resistance of each laminar flow.

When the cross-sectional areas $d_a$ and $d_b$ respectively of the first branch channels 420a and 420b are adjusted to be larger than a cross-sectional area $d_c$ of the first separation channel 410 to obtain a relatively low fluidic resistance in the first branch channels 420a and 420b, compared to the fluidic resistance of the first separation channel 410, a change in fluid flow, such as a back flow, in the first separation unit 400 may be reduced, thereby having a stable inflow of the fluid sample into the second MOFF channel 200a and the third MOFF channel 200b. The inlet of the first MOFF channel 100 may be connected in fluid communication with a sample inlet 10 for introducing the fluid sample to the target particles-separating device. The outlets of the first separation channel 400, and second separation channels 510a and 510b may be connected in fluid communication with one target particle outlet 30 via which the target particles in the fluid sample are collected.

Figure 6:
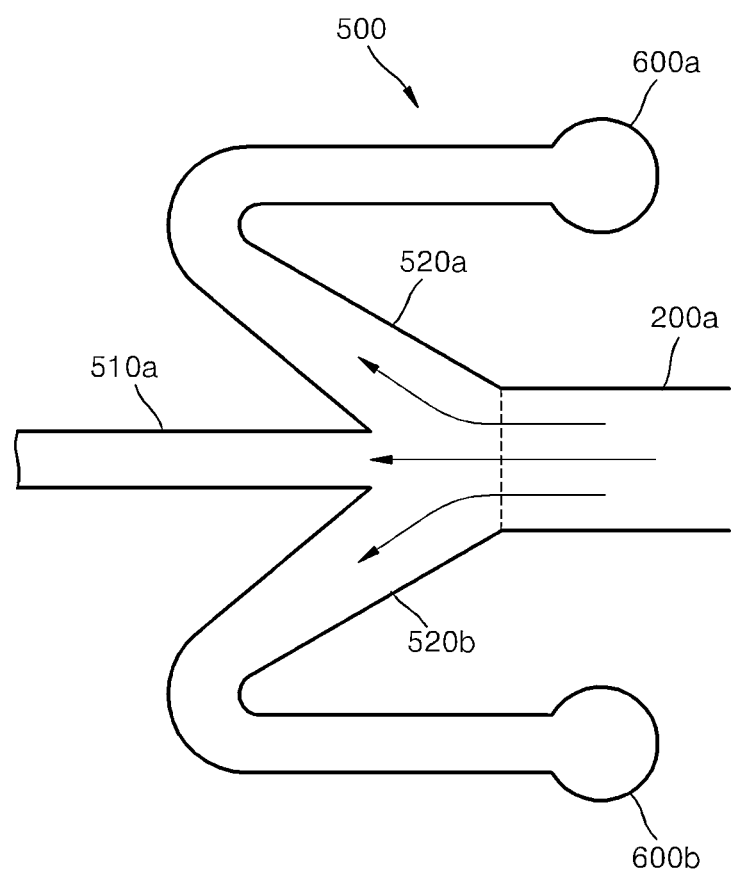
FIG. 6 illustrates an embodiment of a structure of a second separation unit of a target particles-separating device, according to the present disclosure.

FIG. 6 illustrates an embodiment of a portion of a structure of a second separation unit 500 of the target particles-separating device, according to the present disclosure.

According to the illustrated embodiment in FIG. 3, the target particles-separating device may include the second separation unit 500 including the second separation channels 510a and 510b, and second branch channels 520a, 520b, 520c and 520d, where the second separation channels 510a and 510b are interconnected in fluid communication with a center region of the outlet of the second and third MOFF channels 200a and 200b, respectively, the second branch channels 520a, 520b, 520c and 520d interconnected in fluid communication with sidewall regions of the outlet of the second and third MOFF channels 200a and 200b, respectively. Referring to FIG. 6, as the fluid sample is introduced into the second MOFF channel 200a from the first separation unit 400, while passing through the second MOFF channel 200a, relatively large target particles present in the fluid sample are concentrated in the center region of the outlet of the second MOFF channel 200a, and are driven by fluid pressure to travel further along the second separation channel 510a connected in fluid communication with the center region of the outlet of the second MOFF channel 200a. While passing through the second MOFF channel 200a, relatively small target particles present in the fluid sample are concentrated in the sidewall regions of the outlet of the second MOFF channel 200a, and are driven by fluid pressure to travel into the second branch channels 520a and 520b connected in fluid communication with the sidewall regions of the outlet of the second MOFF channel 200a.

The second branch channels 520a and 520b may be connected in fluid communication with waste chambers 600a and 600b for collecting the remnants, excluding the target particles, in the fluid sample, respectively. Thus, the non-separated particles in the fluid sample, remaining not separated to flow into the second separation channel 510a of the second separation unit 500, may be stored in the waste chambers 600a and 600b, or may be discharged out of the target particles-separating device. Although not illustrated in FIG. 6, it would be obvious that as the fluid sample is introduced into the third MOFF channel 200b from the first separation unit 400, target particles may be separated similarly as when the fluid sample is introduced into the second MOFF channel 200a from the first separation unit 400. Similar to the second branch channels 520a and 520b being connected in fluid communication with waste chambers 600a and 600b, for example, remaining second branch channels 520c and 520d may be connected in fluid communication with waste chambers 600c and 600d at distal ends thereof.

Figure 7:
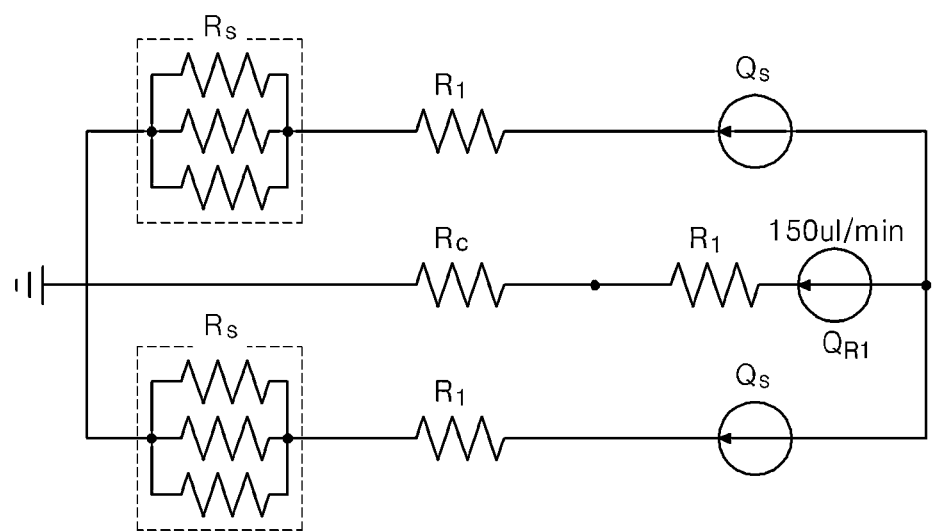
FIG. 7 is an equivalent electrical circuit diagram for describing a fluid flow in the target particles-separating device in FIG. 3.

FIG. 7 is an equivalent electrical circuit diagram for describing fluid flow in the target particles-separating device in FIG. 3.

In general, motions of a small Reynolds number (Re) fluid flow are numerically simulated using Navier-Stokes equations, not taking account into turbulent flow models. Due to having a very low Reynolds number (Re), a fluid flow in a microchannel is considered a laminar flow, not a turbulent flow. Thus, to design the channel structure of FIG. 3, it is convenient to calculate the flow quantity and flow rate of fluid by using a related equivalent electrical circuit. FIG. 7 is an equivalent electrical circuit of the target particles-separating device of FIG. 3. To manufacture the target particles-separating device of FIG. 3, the following conditions are necessary.

Referring to FIGS. 3 and 7, fluid resistors $R_1$ may indicate fluidic resistance in the first, second, and third MOFF channels 100, 200a, and 200b, a fluid resistor $R_c$ may indicate fluidic resistances in the first separation channel 410, $Q_s$ may indicate a flow quantity of the buffer supplied from the buffer inlet, a fluid resistor $R_s$ may indicate fluidic resistance in the second separation unit 500, and $Q_{R1}$ indicates a flow quantity and flow rate the fluid sample entering the first MOFF channel 100. $Q_{R1}$ is assumed to be 150 microliters per minute (μl/min). In the equivalent electrical circuit, a flow quantity across the fluid resistors $R_1$ of the first, second, and third MOFF channels 100, 200a, and 200b may be consistent, for example, as 150 μl/min with the assumption that a Reynolds number (Re) is 90. A flow quantity $Q_{Rc}$ across the fluid resistor $R_c$ of the first separation channel 410 may be about 20% of the flow quantity $Q_{R1}$ across the fluid resistors $R_1$ of the first, second, and third MOFF channels 100, 200a, and 200b. A fluidic resistance of the fluid resistor $R_s$ of the second separation unit 500 may be negligibly small relative to that of the fluid resistor $R_1$ of the first, second, or third MOFF channels 100, 200a, and 200b (Rs<<$R_1$). With the assumption of the above conditions, the following equations may be obtained.

$$R_c = 5R_1 \quad \text{Equation 1}$$

$$Q_s = (2Q_{R1} + Q_{Rc} - Q_{R1})/2 = (Q_{R1} + 0.2Q_{R1})/2 = 0.6Q_{R1} \quad \text{Equation 2}$$

If the fluidic resistance of the fluid resistor $R_c$ is given, the fluidic resistances of the fluid resistors $R_1$ may be calculated, and a cross-sectional area of the first branch channels 420a and 420b may be determined. In laminar flows, the fluidic resistance of a rectangular cross-section channel may be determined using a known equation. For example, whether a flow is laminar or turbulent may be determined by Equation 3 below, a resistance of laminar flow in the channel may be determined by Equation 4 below, a hydraulic diameter of a non-circular, rectangular channel may be determined by Equation 5 below, and a shape compensation coefficient of a non-circular, rectangular channel may be determined by Equation 6.

$$\text{Re} = \frac{\rho V D}{\mu} \quad \text{Equation 3}$$

$$R = \frac{f\text{Re}}{2} \frac{\mu l}{D_h^2 A} \quad \text{Equation 4}$$

$$D_h = 4\frac{\text{Area}}{\text{Perimeter}} = \frac{2ab}{(a+b)} \quad \text{Equation 5}$$

$$f\text{Re} = 96(1 - 1.3553\alpha + 1.9467\alpha^2 - 1.7012\alpha^3 + 0.9564\alpha^4 - 0.2537\alpha^5) \quad \text{Equation 6}$$

Parameters in Equations 3-6 are defined as follows: ρ: fluid density of water in kilograms per cubed meter (kg/m$^3$), V: average fluid velocity in meters per second (m/s), μ: dynamic viscosity in Newton second per square meters (N·s/m$^2$), $D_h$: hydraulic diameter in meters (m), A: area of the channel cross section (m$^2$), and fRe: shape constant.

EXAMPLES

1. Design and Manufacture of a Particles-Separating Device

The particles-separating device of FIG. 3 was fabricated by soft-lithography techniques. A 6-inch silicon wafer was used as a substrate, and SU-8 (SU-8 2050, available from Micro-Chem Corporation, Massachusetts, United States) was used for a channel master mold. A pattern of the particles-separating device was replicated with polydimethylsiloxane ("PDMS") (SYLGARD® 184, available from Dow Corning Corporation, Michigan, United States). A volumetric mixture of PDMS and a curing agent at a ratio of about 10:1 was poured on the channel master mold, and followed by degassing the mixture and placing the wafer on a hot plate at about 75 degrees Celsius (° C.) for about 60 minutes. A cured polymer mixture was removed from the channel master mold and was punched to form an inlet and an outlet, and bonded to a glass after plasma treatment using a plasma generator (Cute-B Plasma system, available from FEMTO Science, Korea), thereby manufacturing the particles-separating device.

The first, second, and third MOFF channels 100, 200a and 200b of the particles-separating device each include an inlet, a filter, a multi-orifice segment, and an outlet. The multi-orifice segment includes an alternating series of eighty (80) contraction channels and eighty (80) expansion chambers, each contraction channel having a width of about 40 μm and a length of about 100 μm, each expansion chamber having a width of about 200 μm and a length of about 200 μm, and both having a thickness of about 40 μm. In the particles-separating device, the first separation channel 410 of the first separation unit 400 may have a width of about 40 μm and a length of about 40 mm, and the first branch channels 420a and 420b may each have a width of about 1 mm and a length of about 10 mm.

2. Preparation of Sample Solution

For particles separation tests, a sample solution was prepared in a 0.5 wt % TWEEN® 20 (available from Sigma-Aldrich Co., Missouri, United States) aqueous solution. To test whether it is possible to separate particles by size by using the particles-separating device, three different sample solutions were prepared: sample solution 1 including fluorescent polystyrene microspheres having a diameter of about 15 μm (available from Thermo Fisher Scientific Inc., Mfr. No. 36-4, red, 542/612 nm), sample solution 2 including fluorescent polystyrene microspheres having a diameter of about 7 μm (available from Thermo Fisher Scientific Inc., Mfr. No. 35-2, green, 468/508 nm), and sample solution 3, which is a mixture of the sample solutions 1 and 2. To test whether it is possible to separate biological particles by size by using the particles-separating device, two different sample solutions were prepared: sample solution 4 including 1,000 MCF-7 cells/μl, and sample solution 5, which is a mixture of the sample solution 4 and 50,000 RBCs/μl.

3. Experimental Methods

A syringe pump (KDS200, available from KD Scientific, Massachusetts, United States) was used to generate a continuous and stable micro flow in the particles-separating device. Particles separation tests were conducted with a 1 milliliter (mL) syringe pump connected to the sample inlet 10 for the sample solution, and 10 mL syringe pumps connected to the buffer inlets 20a and 20b for buffer. The flow rate of the sample solution at the sample inlet 10 was set to about 120 μl/min, taking into account the Reynolds number of the multi-orifice segments (Re=85). To reduce experimental errors, degassing from the particles-separating device was conducted with 70% ethanol. An inverted optical microscope (I-70, available from Olympus, Japan) and a CCD camera (ProgRes C10, available from JENOPTIK, Germany) were used to measure fluorescent signals from the flow of particles in the particles-separating device.

4. Experimental Results

Figure 8:
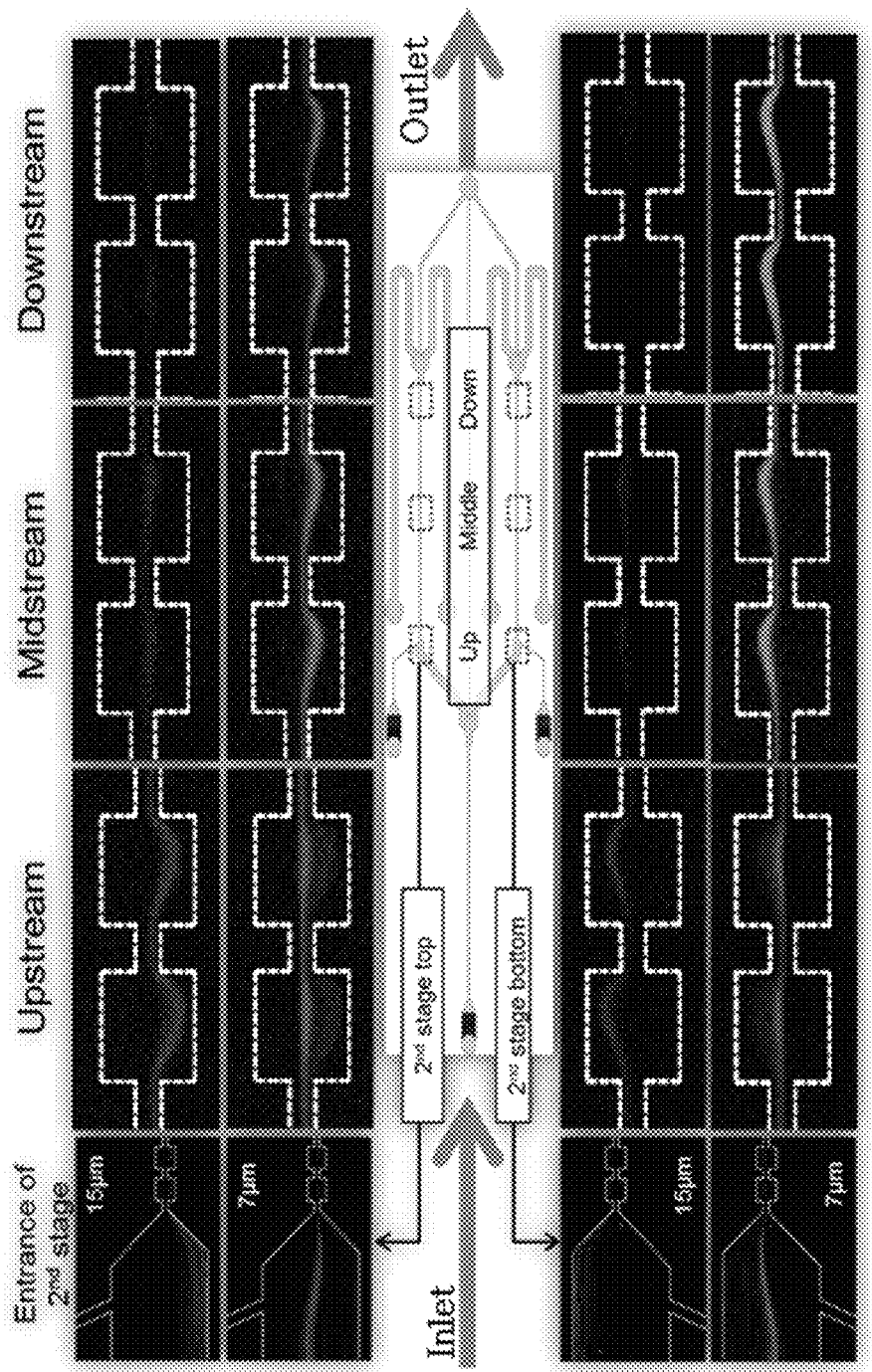
FIGS. 8 to 12 illustrate the results of observing flows of different sample solutions in the target particles-separating device in FIG. 3.

FIG. 8 illustrates flows of the sample solutions 1 and 2 in the second and third MOFF channels 200a and 200b of the particles-separating device. Particles distributions in the sample solutions 1 and 2 at the $1^{st}$ (upstream), $40^{th}$ (midstream), and $80^{th}$ (downstream) orifices of the second and third MOFF channels 200a and 200b were fluorescently captured. As a result, particle separation began to occur around the $35^{th}$ to $45^{th}$ orifices, and stable particle distribution was observed at around the $70^{th}$ to $80^{th}$ orifices. About 7 μm particles in the sample solution 2 were observed to cluster near both sidewall regions in the first MOFF channel 100, but to only one sidewall region in the second and third MOFF channels 200a and 200b. This is attributed to that the 7 μm particles tend to only flow near one sidewall region, and are biased to one sidewall region as the buffer flows in from the buffer inlet. The biased particles are found to be continuously biased to the same sidewall region until the end of the multi-orifice segment.

On the other hand, about 15 μm particles in the sample solution 1 are found to cluster around the center region of the multi-orifice segment at Re=85. Referring to a $2^{nd}$ stage top image of FIG. 8, relatively large particles (15 μm, red) are found to cluster much around the center region of the second MOFF channel 200a of the target particles-separating device, away from the inlet of the second MOFF channel 200a, while relatively small particles (7 μm, green) tend to cluster much near the sidewall region of the second MOFF channel 200a. Referring to a $2^{nd}$ stage bottom image of FIG. 8, relatively large particles (15 μm, red) are found to cluster much around the center region of the third MOFF channel 200b of the particles-separating device, away from the inlet of the third MOFF channel 200b, while relatively small particles (7 μm, green) tend to cluster much near the sidewall region of the third MOFF channel 200b.

Figure 9:
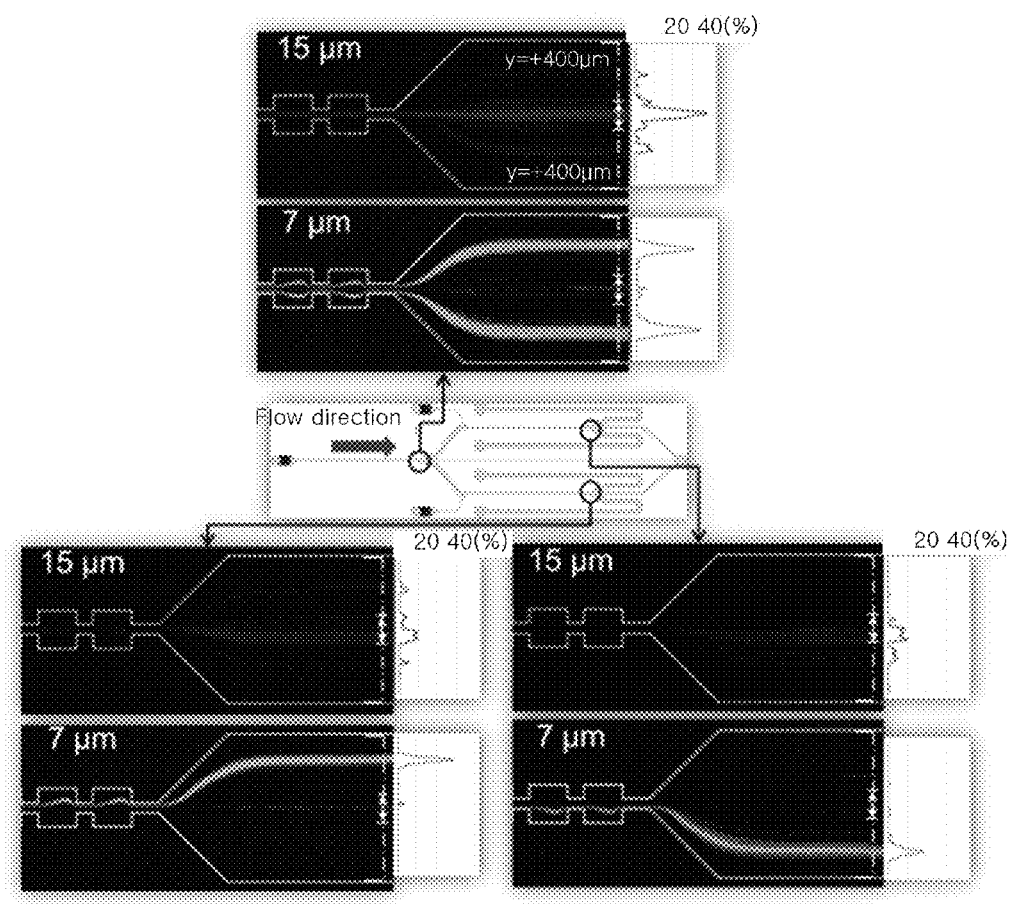

FIG. 9 illustrates flows of the sample solutions 1 and 2 in the first and second separation unit 500 of the target particles-separating device. Referring to a $1^{st}$ stage top image of FIG. 9, relatively large particles (15 μm, red) are found to cluster around the center region of the first separation unit 400 of the target particles-separating device, while relatively small particles (7 μm, green) tend to cluster near the sidewall regions of the first separation unit 400. Referring to a $2^{nd}$ stage bottom image of FIG. 9, relatively large particles (15 μm, red) are found to cluster around the center region of the second separation unit 500 of the target particles-separating device, while relatively small particles (7 μm, green) tend to cluster near the sidewall regions of the second separation unit 500. In particular, about 15 μm particles are found to concentrate near the center region of each MOFF channel 100, 200a and 200b (about 140 μm inwards from the sidewall region of the 800 μm-wide outlet), while about 7 μm particles concentrate in the sidewall region of each MOFF channel 100, 200a and 200b (away from the 140 μm-inward center region of the 800 μm-wide outlet). The particles in the sample solution flow from the first MOFF channel 100 into the second and third MOFF channels 200a and 200b, thereby branching off from the first MOFF channel 100, and are diluted with a supply of a buffer, thus showing a reduced fluorescence in the second and third MOFF channels compared to that in the first MOFF channel. After passing through the first MOFF channel 100, about 15 μm particles are mostly separated in the first separation unit 100, thus showing a relatively low fluorescence in the second and third MOFF channels 200a and 200b compared to that of about 7 μm particles (e.g., fluorescence of about 15 μm particles in the second and third MOFF channels 200a and 200b is about 23% of that in the first MOFF channel 100, and the fluorescence of about 7 μm particles in the second and third MOFF channels 200a and 200b is about 72% of that in the first MOFF channel 100).

Figure 10:
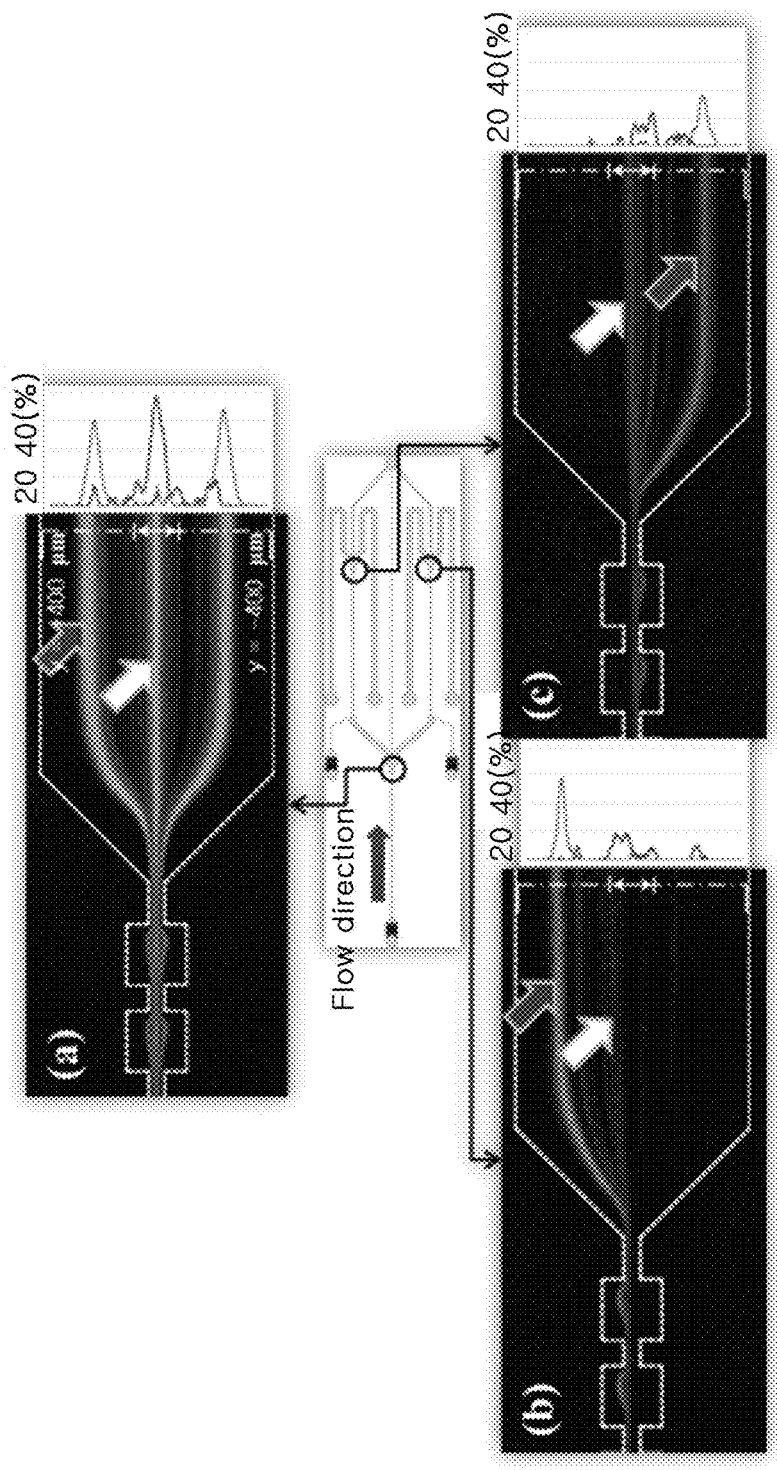

FIG. 10 illustrates flows of the sample solution 3 in the first and second separation units 400 and 500 of the target particles-separating device. Fluorescent images of FIG. 10 were acquired using a green fluorescent filter cube (U-MWB2, available from Olympus, Japan) so that red images may look yellow when two red and green colors are presented at the same time. Referring to a $1^{st}$ stage top image of FIG. 10, relatively large particles (15 μm, white arrows) are found to cluster around the center region of the first separation unit 400 of the target particles-separating device, while relatively small particles (7 μm, dark arrows) tend to cluster near the sidewall region of the first separation unit 400. Referring to a $2^{nd}$ stage bottom image of FIG. 10, relatively large particles (15 μm, white arrows) are found to cluster around the center region of the second separation unit 500 of the target particles-separating device, while relatively small particles (7 μm, dark arrows) tend to cluster near the sidewall region of the second separation unit 500. Thus, similar results as those in FIG. 9, obtained from the sample solutions each including single-size particles, may be obtained with the mixed sample solution of particles having different sizes.

According to analytical results, when using a single MOFF channel by controlling a Reynolds number (Re), recovery of about 15 μm particles may be increased from about 65% to about 75.2%, while purity of the particles may be considerably reduced from about 90.8% to about 49.6%. However, when using the embodiments of the target particles-separating device and method according to the present disclosure, recovery of about 15 μm particles may be increased from about 73.2% to about 88.7% with a constant Reynolds number (Re), while purity is slightly reduced from about 91.4% to about 89.1%. In the embodiments of the target particles-separating device and method according to the present disclosure, with an increased number of MOFF channels, about 100% recovery and about 90% or greater purity may be achieved, raising an expectation of applications in various fields.

Figure 11:
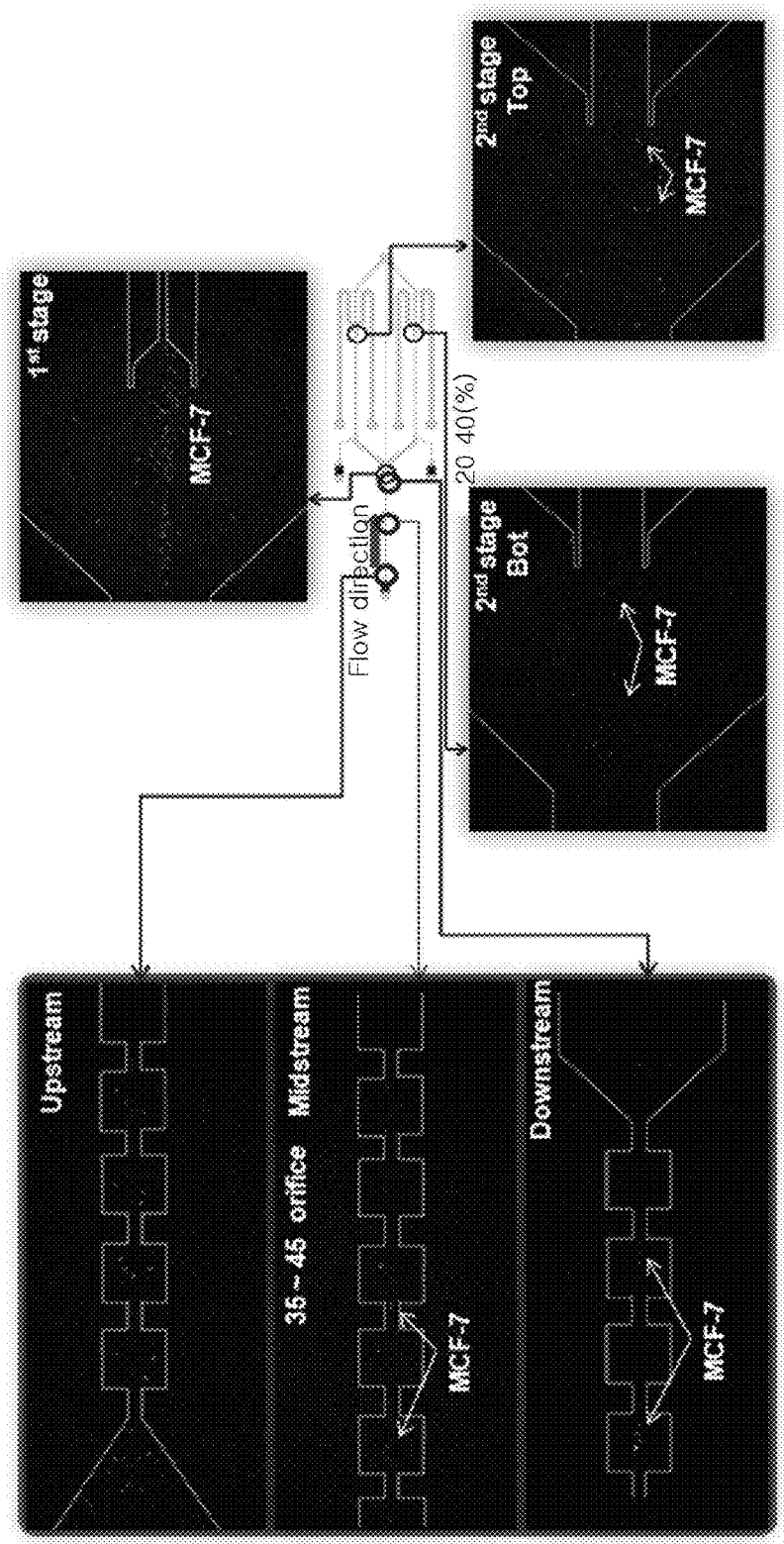

FIG. 11 illustrates flows of the sample solution 4 in the first MOFF channel 100, the first separation unit 400, and the second separation unit 500 of the target particles-separating device. Referring to the left-side images (upstream, midstream, and downstream) of FIG. 11, the MCF-7 cells are found to cluster near the center region of the first MOFF channel 100, beginning from the $35^{th}$ to $45^{th}$ orifice regions of the first MOFF channel 100. Referring to a right-side $1^{st}$ stage top image of FIG. 11, MCF-7 cells are found to cluster near the center region of the first separation unit 100. A right-side $2^{nd}$ stage bottom view of FIG. 11 shows that MCF-7 cells also cluster near the center region of the second separation unit 500.

Figure 12:
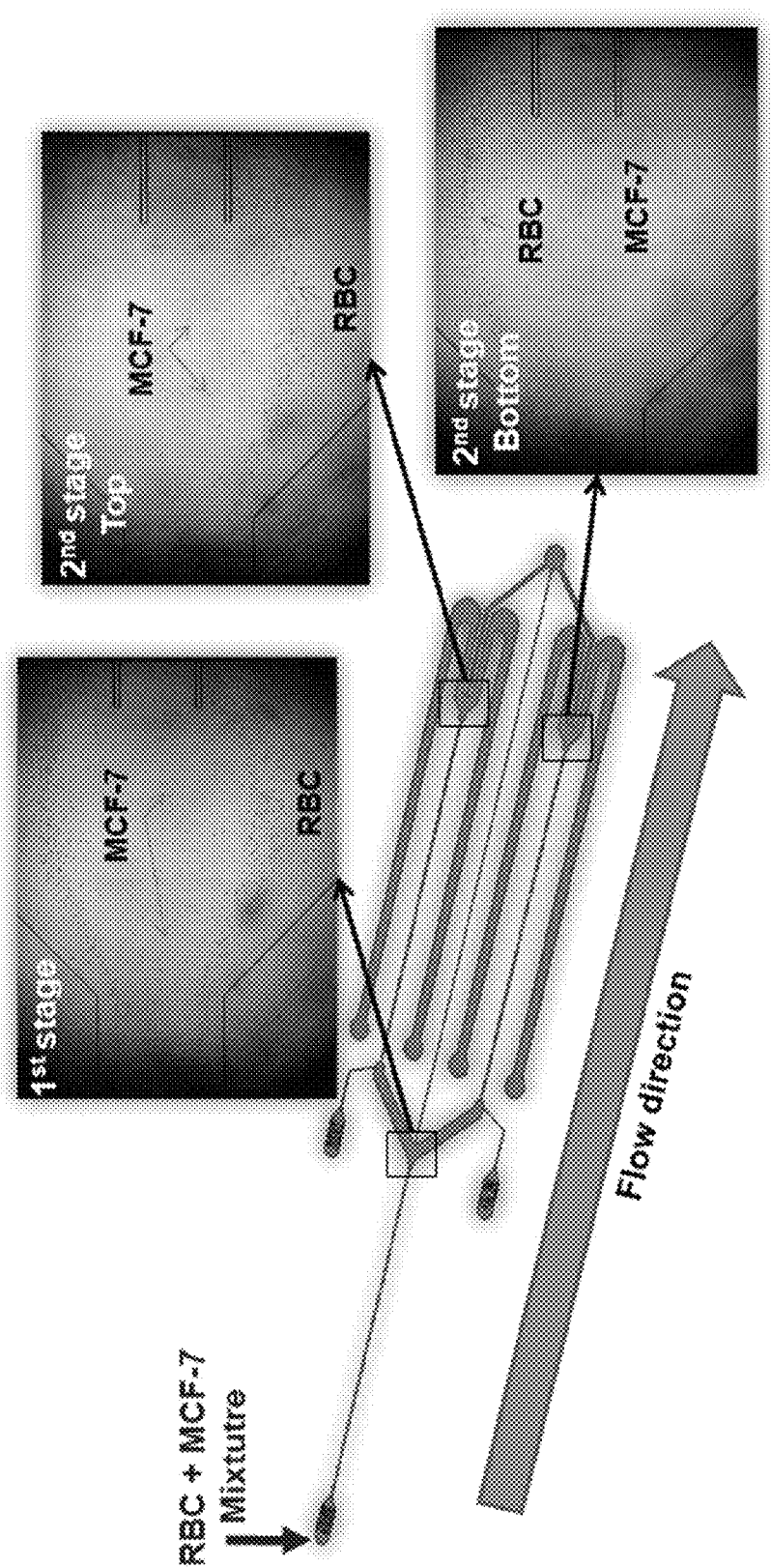

FIG. 12 illustrates flows of the sample solution 5 in the first and second MOFF channels 100, 200a and 200b of the target particles-separating device. Referring to a center $1^{st}$ stage top image of FIG. 12, the MCF-7 cells are found to cluster near the center region of the first separation unit 400, while RBCs, smaller than the MCF-7 cells, cluster near the sidewall regions of the first separation unit 400. Referring to right-side $2^{nd}$ stage top and bottom images of FIG. 12, MCF-7 cells are found to cluster near the center region of the second separation unit 500, while RBCs, smaller than the MCF-7 cells, cluster near the sidewall regions of the second separation unit 500.

As described above, according to the one or more of the above embodiments of the present disclosure, by using a target particles-separating device and method using an MOFF channel, target particles in a fluid sample may be efficiently separated.

It should be understood that the embodiments described herein should be considered in a descriptive sense only and not for purposes of limitation. Descriptions of features within each embodiment should typically be considered as available for other similar features or aspects in other embodiments.

What is claimed is:

1. A device for separating target particles in a fluid sample, the device comprising:
    a first, second and third multi-orifice flow fractionation channel, each including:
        a multi-orifice segment with an inlet and an outlet at opposite ends, the multi-orifice segment including an alternating series of contraction channels and expansion chambers interconnected in a lengthwise direction,
        wherein dimensions of the contraction channels and expansion chambers are defined based on a size of the target particles;
    a first separation unit including:
        a first separation channel which is interconnected in fluid communication with a center region of the outlet of the first multi-orifice flow fractionation channel, and
        first branch channels which are interconnected in fluid communication with sidewall regions of the outlet of the first multi-orifice flow fractionation channel, and respectively with the inlets of the second and third multi-orifice flow fractionation channels; and
    buffer inlets which are connected to the inlets of the second and third multi-orifice flow fractionation channels and through which a buffer flows into the second and third multi-orifice flow fractionation channels.

2. The device of claim 1, wherein the first separation channel has a relatively large fluidic resistance compared to a fluidic resistance of the first branch channels, the fluid resistances based on dimensions of the first separation channel and the first branch channels.

3. The device of claim 1, wherein a cross-sectional area of the first separation channel is relatively small compared to a cross-sectional area of the first branch channels.

4. The device of claim 1, further comprising a second separation unit including:
    a second separation channel which is interconnected in fluid communication with a center region of the outlet of each of the second and third multi-orifice flow fractionation channels, and
    second branch channels which are interconnected in fluid communication with a sidewall region of the outlet of each of the second and third multi-orifice flow fractionation channels.

5. The device of claim 4, further comprising waster chambers which are interconnected in fluid communication with the second branch channels, wherein the waste chambers collect non-selected particles excluding the target particles in the fluid sample.

6. The device of claim 1, further comprising a sample inlet which is interconnected in fluid communication with the inlet of the first multi-orifice flow fractionation channel, and through which the fluid sample is introduced.

7. The device of claim 5, further comprising one target particle outlet via which is interconnected in fluid communication with outlets of the first separation channel and the second separation channel, and in which the target particles in the fluid sample are collected.

8. The device of claim 5, wherein the first separation channel has a fluidic resistance which is about five times as large as a fluidic resistance of the first, second, and third multi-orifice flow fractionation channels, the fluid resistances based on dimensions of the first separation channel and the first, second, and third multi-orifice flow fractionation channels.

9. A method of separating target particles in a fluid sample, the method comprising:
    providing a plurality of multi-orifice flow fractionation channels, each including:
        a multi-orifice segment with an inlet and an outlet at opposite ends, the multi-orifice segment including an alternating series of contraction channels and expansion chambers interconnected in a lengthwise direction,
        wherein dimensions of the contraction channels and expansion chambers are defined based on a size of the target particles;
    introducing a first fluid sample including the target particles into the inlet of a first multi-orifice flow fractionation channel;
    collecting target particles discharged from a center region of the outlet of the first multi-orifice flow fractionation channel to separate the target particles from the first fluid sample;
    introducing a second fluid sample discharged from sidewall regions of the outlet of the first multi-orifice flow fractionation channel into the inlet of a second multi-orifice flow fractionation channel; and
    collecting target particles discharged from a center region of the outlet of the second multi-orifice flow fractionation channel to separate the target particles from the second fluid sample.

10. The method of claim 9, wherein the introducing the second fluid sample discharged from the sidewall regions of the outlet of the first multi-orifice flow fractionation channel into the inlet of the second multi-orifice flow fractionation channel comprises:
    introducing a buffer into the inlet of the second multi-orifice flow fractionation channel so that a total fluid quantity introduced into the inlet of the second multi-orifice flow fractionation channel is consistent with a quantity of the first fluid sample introduced into the inlet of the first multi-orifice flow fractionation channel.

11. The method of claim 9, wherein the introducing the second fluid sample discharged from the sidewall region of the outlet of the first multi-orifice flow fractionation channel into the inlet of the second multi-orifice flow fractionation channel comprises:
    introducing a buffer into the inlet of the second multi-orifice flow fractionation channel so that a total fluid quantity introduced into the inlet of the second multi-orifice flow fractionation channel is different from a quantity of the first fluid sample introduced into the inlet of the first multi-orifice flow fractionation channel.

12. A device for separating target particles in a fluid sample, the device comprising:
    a plurality of multi-orifice flow fractionation channels which are connected in series, each including a multi-orifice segment with an inlet and an outlet at opposite ends, the multi-orifice segment including an alternating series of contraction channels and expansion chambers interconnected in a lengthwise direction between the inlet and outlet, a single target particle outlet which collects separated target particles from the fluid sample which passes through each of the plurality of multi-orifice flow fractionation channels; and a separation unit including:
an inlet which is in direct fluid communication with each of the outlets of the plurality of orifice flow fractionation channels, and
an outlet which is in direct fluid communication with the single target particle outlet;
wherein the separation unit
passes the target particles from a center of the outlets of the plurality of orifice flow fractionation channels to the target particle outlet, and
passes non-target particles from a sidewall region of the outlets of the plurality of orifice flow fractionation channels away from the target particle outlet.

13. The device of claim 12, wherein the separation unit further comprises:
a separation channel through which the target particles from the center of the outlets of the plurality of orifice flow fractionation channels flow to the target particle outlet; and
a branch channel through which the non-target particles from the sidewall region of the outlets of the plurality of orifice flow fractionation channels flow away from the target particle outlet.

14. The device of claim 13, wherein a cross-sectional area of the separation channel is relatively small compared to a cross-sectional area of the branch channel.

* * * * *